United States Patent [19]

Iino et al.

[11] Patent Number: 4,764,201
[45] Date of Patent: Aug. 16, 1988

[54] PLANT GROWTH REGULATION

[75] Inventors: Yasuo Iino; Yoshinori Saito, both of Iwaki, Japan

[73] Assignee: Tomoe Kagaku Kogyo Kabushiki Kaisha, Fukushima, Japan

[21] Appl. No.: 712,751

[22] Filed: Mar. 18, 1985

[51] Int. Cl.$^4$ .................. H01N 31/08; H01N 33/06; H01N 43/40; H01N 43/16

[52] U.S. Cl. .................................... 71/77; 71/88; 71/86; 71/94; 71/103; 71/181; 71/106

[58] Field of Search .................... 71/77, 123, 121, 86, 71/103, 106, 88

[56] References Cited

U.S. PATENT DOCUMENTS 2,435,499  2/1948  Nadd ........................... 71/123

FOREIGN PATENT DOCUMENTS 75841  6/1978  Japan .

OTHER PUBLICATIONS

Murrhy et al. Chem. Abst. vol. 96 (1982) 121123h.

*Primary Examiner*—Catherine L. Mills
*Attorney, Agent, or Firm*—Wenderoth, Lind & Ponack

[57] ABSTRACT

Certain water-soluble derivatives of vitamin K compounds have been found to regulate the growth of plants. The present invention relates to a method for plant growth regulation with such water-soluble derivatives of vitamin K compounds and plant growth regulating compositions comprising the same.

9 Claims, No Drawings

PLANT GROWTH REGULATION

BACKGROUND OF THE INVENTION

The present invention relates to the use of certain water-soluble derivatives of vitamin K compounds. More particularly, the invention relates to a method for plant growth regulation with such water-soluble derivatives of vitamin K compounds and plant growth regulating compositions comprising the same.

It is highly profitable from the economical point of view to hasten the harvesttime or to enhance the yield of plants by accelerating the growth of the plants.

We have conducted intensive investigations to develop plant growth regulating compositions from among drugs, food additives, feed additives and the like which have been evaluated as innoxious. As a result, we have unexpectedly found that, by applying water-soluble derivatives of vitamin K compounds to cereals such as rice plants, a variety of garden plants such as fruit vegetables, leaf vegetables, and root vegetables, flowers and ornamental plants, and fruit trees, the growth of the shoots or tops and/or roots of the plants is notably accelerated as compared with that in the case where no such compounds are applied. On the basis of this finding, we have arrived at the present invention.

SUMMARY OF THE INVENTION

The present invention provides a method for regulating the growth of plants which comprises applying to the foliage, roots, stems, and seeds of the plants and/or to the soil or hydroponic medium in which the plants are grown an effective plant growth regulating amount of at least one water-soluble derivative of a vitamin K compound.

This invention further provides a plant growth regulating composition comprising a water-soluble derivative of a vitamin K compound as an active ingredient and an agriculturally acceptable adjuvant.

DETAILED DESCRIPTION OF THE INVENTION

The water-soluble derivatives of vitamin K compounds used in the present invention are known as antihemorrhagic vitamins. Examples of such derivatives are: menadione bisulfites such as menadione sodium bisulfite and menadione dimethylpyrimidinol bisulfite; menadiol inorganic acid ester salts such as menadiol tetrasodium diphosphate, menadiol disodium disulfate, and menadiol dipotassium disulfate; menadiol organic acid esters such as menadiol diacetate; menadiol organic acid ester salts such as menadiol dinicotinate dihydrochloride; menadiol organic acid ester quaternary ammonium salts such as menadiol bis(trimethylammonium acetate)dichloride; menadiol bis(glucoside tetraacetate); 4-amino-2-methyl-1-naphthol hydrochloride; 4-amino-3-methyl-1-naphthol hydrochloride; and 1,4-diamino-2-methylnaphthalene dihydrochloride.

The compounds of the invention, water-soluble derivatives of vitamin K compounds, are known substances which can be easily prepared by conventional methods employed in organic chemistry. Some examples of such methods are disclosed in J. Amer. Chem. Soc., 62, 228(1940); ibid., 63, 2049(1941); ibid., 64, 2659(1942); ibid., 64, 2661(1942);U.S. Pat. No. 2,372,655; and U.S. Pat. No. 2,428,253. Further, menadione sodium bisulfite and menadione dimethylpyrimidinol bisulfite which are typical examples of the water-soluble derivatives of vitamin K compounds are available commercially and are widely used as drugs and feed additives.

The water-soluble derivatives of vitamin K compounds, one or more thereof, can be used singly but are ordinarily admixed with various adjuvants commonly added to agricultural chemicals including carriers, diluents, extenders and conditioning agents to form granules, wettable powders, pellets, dusts, tablets, solutions, dispersions or emulsions depending upon the purpose.

The proportion of the compounds of the present invention incorporated in such compositions is from 0.1 to 99.9% (by weight, as in all percentages and parts set forth hereinafter), preferably from 0.5 to 85%.

The carrier may be in either liquid or solid form, illustrative solid carriers being clays, talcs, diatomaceous earth, kaolin, bentonite and the like, while typical liquid carriers are water, methanol and the like.

As the adjuvant for improving the dispersing, suspending, wetting, adhering and penetrating properties as well as the emulsifiability of the composition, ionic or nonionic surfactants, high polymers such as carboxymethyl cellulose, polyvinyl alcohol and sodium alginate, and the like can be used.

If necessary, other inorganic salts, inorganic fertilizers, organic fertilizers, insecticides, fungicides and herbicides may also be added to the composition or used in combination therewith.

The water-soluble derivatives of vitamin K compounds are applicable for the purpose of regulating the growth of a wide variety of plants. Among the plants to which the compounds of the present invention are applicable are: farm products such as rice plants, barley, wheat, oats, peas, soybeans, potatoes, sweet potatoes, and corn; vegetables such as cucumbers, eggplants, tomatoes, Chinese cabbages, Welsh onions, head lettuces, spinaches, Japanese radishes, edible burdocks, and carrots; flowers such as chrysanthemums, carnation and crocuses; trees such as cryptomeria and Japanese cypress (hinoki); lawns; and fruit trees such as mandarins, apples, pears, peaches, and grapes.

The water-soluble derivatives of vitamin K compounds can be applied at any stage of the growth of plants. The compounds of the present invention may be applied at the seed stage, for example, by soaking the seed in a solution containing the compounds or coating the seed with the solution in combination with an appropriate coating agent. The compounds may also be sprayed or coated over the foliage, flower or fruit of plants at the seedling stage, flowering stage or seed-setting stage thereof, or otherwise may be applied to plants sequentially at one or more stages of growth. The compounds may further be applied to the soil or hydroponic medium in which plants are grown.

The precise rates of application of the compounds of the present invention are dependent upon the species of the plant to be treated, the specific portion of the plant to which the compounds are applied, the district in which the plant is grown, the stage of the growth of the plant, the mode of application and various other factors, so that the compounds should be applied in an appropriate rate selected with due consideration for such factors. Generally, the compounds are applied at a rate of from 2 to 20,000 g per acre, preferably from 10 to 10,000 g per acre, as the effective ingredient.

While the concentration of the solution may vary in a considerably wide range, a concentration of generally from 0.001 to 100,000 ppm, preferably from 0.01 to 5,000 ppm, is employed.

The growth of plants treated with the plant growth regulating compositions of this invention was found to be accelerated as compared with untreated plants. In particular, the development of the root system and the increase of the fresh weight were remarkable, which would contribute to early-season harvests, and increased yields. For example, the application of the compositions to plants requiring transplantation such as rice plants encourages rooting and striking whereby highly stable harvests can be expected. The compositions of the present invention which exhibits remarkable activity under low temperature conditions are especially noteworthy in ensuring strong resistance of seedlings to the phenomenon of lowering of season average temperatures which is observed in recent years and is called "abnormal weather conditions".

In order to indicate more fully the nature and utility of this invention, the following specific examples of practice are set forth, it being understood that these examples are presented as illustrative only and not intended to limit the scope of the invention.

EXAMPLE 1

1 part of menadione sodium bisulfite, 1 part of Tween 20 ® (surfactant supplied by Kao Atlas K.K., Japan) and 98 parts of diatomaceous earth were thoroughly mixed to obtain a dust formulation.

EXAMPLE 2

A liquid formulation was prepared from 5 parts of 4-amino-2-methyl-1-naphthol hydrochloride and 95 parts of water.

EXAMPLE 3

10 parts of menadiol diacetate, 88 parts of clay and 2 parts of sodium dodecylbenzene sulfonate were thoroughly mixed to obtain a wettable powder.

EXAMPLE 4

The compounds of the present invention and the solid carriers listed in Table 1 were thoroughly mixed in the ratios set forth in the Table to obtain a dust formulation.

TABLE 1

| Compound | Part by weight | Carrier | Part by weight |
| --- | --- | --- | --- |
| menadione dimethyl-pryimidinol bisulfite | 5 | diatomaceous earth | 50 |
| | | clay | 45 |
| menadiol tetrasodium diphosphate | 2 | diatomaceous earth | 40 |
| | | talc | 58 |
| menadiol disodium disulfate | 2 | talc | 50 |
| | | kaolin | 48 |
| 4-amino-3-methyl-1-naphthol hydrochloride | 2 | talc | 48 |
| 1,4-diamino-2-methyl-naphthalene dihydrochloride | 1 | talc | 99 |
| menadiol dinicotinate dihydrochloride | 1 | clay | 99 |

EXAMPLE 5

1 acre/400000 Neubauer's pots were each charged with a mixture of 500 g of soil, 3 g of Tomoe Kasei Special No.8 (fertilizer, N—P₂O₅—K₂O (6:7:7)) and a prescribed quantity of a dust formulation prepared as in Example 1. Each of the pots was seeded with 20 germination-hastened rice plant seeds which were then grown in a greenhouse at 25° C. for 15 days. Two runs of experiments were carried out respectively in the test plot and control plot. The plant lengths and main root lengths of the treated plants were measured to obtain the ratios thereof to those of the untreated plants. The results are shown in Table 2 below.

TABLE 2

| Experimental Plot | Increase in Height (%) | Main Root Length (%) |
| --- | --- | --- |
| Untreated | 100 | 100 |
| Treated | | |
| dust formulation 0.5 g/pot | 109 | 108 |
| dust formulation 1 g/pot | 132 | 122 |
| dust formulation 2 g/pot | 109 | 115 |
| dust formulation 3 g/pot | 100 | 110 |

Note:
The average height and main root length of the untreated plants were 5.90 cm and 7.56 cm, respectively As is indicated in Table 2, the growths of the shoots or tops and roots of the plants treated with the dust formulation of the present invention were apparently accelerated.

EXAMPLE 6

Into 20-mm diam. test tubes were poured menadione sodium bisulfite solutions respectively having active ingredient concentrations of 10 ppm and 100 ppm. The second-leaf-stage seedlings of rice plants with the primary root thereof cut off except for the base portion 1 mm high were fixed with absorbent cotton around the stem portion thereof so that the seedlings would be disposed 1 cm below the surface of each solution. After growing the seedlings at 30° C. under continuous irradiation at 3,300 lux for 8 days, the maximum root lengths of the seedlings were measured to obtain the ratios thereof to those of the untreated seedlings. The results are set forth in Table 3.

TABLE 3

| Concentration (ppm) | Max. root length (%) |
| --- | --- |
| Untreated | 100 |
| Treated | |
| 10 | 160 |
| 100 | 129 |

Note:
The average maximum root length of the untreated seedlings was 43.4 mm.

As is apparent from Table 3, the treatment with menadione sodium bisulfite solution encourages rooting of the rice plant seedlings.

EXAMPLE 7

Nursery boxes each of a size of 30×60×5 cm were filled with Pilomat ® (medium for raising seedlings, supplied by Marusan Seishi K.K., Japan) as seedling beds, to which 4 g, 8 g and 16 g, respectively, of a dust formulation prepared as in Example 1 were added. Subsequently, each of the boxes was seeded with 210 g of germination-hastened paddy rice seeds (Sasanishiki) which were covered with soil for growing seedlings. The seedlings were caused to emerge at 32° C. for 2 days, greened at 25° C. for another 2 days, and then hardened in a greenhouse. 21 days after seeding, the traits of the young seedlings were examined, and the results shown in Table 4 were obtained.

On the same day, 4 seedlings per clump were transplanted into 1 acre/200000 pots which were placed in a biotron having a high temperature area (day/night temperatures: 25° C./17° C.) and a low temperature limit area (day/night temperatures: 17° C./12° C.) to promote striking 7 days after transplanting, the seedlings were sampled to examine the degree of striking. The data obtained by the striking tests in the high temperature area and the low temperature limit area are summarized respectively in Table 5 and Table 6.

TABLE 4

| Experimental Plot | Traits of Young Seedlings | | | |
|---|---|---|---|---|
| | Seedling Age | Height (mm) | Dry Weight of tops (mg) | Number of Roots |
| Untreated | 3.1 | 107.0 | 17.4 | 8.6 |
| Treated | | | | |
| dust formulation 4 g/case | 3.2 | 102.0 | 18.8 | 9.9 |
| dust formulAtion 8 g/case | 3.1 | 103.4 | 18.7 | 8.9 |
| dust formulation 16 g/case | 3.1 | 99.4 | 17.5 | 9.4 |

As is apparent from Table 4, the seedlings treated with the dust formulation of the present invention were shorter in height than the untreated seedlings but were improved in dry weight of tops and number of roots.

TABLE 5

| Experimental Plot | Striking Tests Under High Temperature Conditions | | | | |
|---|---|---|---|---|---|
| | Seedling Age | Height (mm) | Total Number of Roots | Number of Fresh Roots | Max. Root Length (mm) |
| Untreated | 3.7 | 117.0 | 14.0 | 8.0 | 87.0 |
| Treated | | | | | |
| dust formulation 4 g/case | 3.7 | 112.6 | 15.4 | 9.4 | 95.3 |
| dust formulation 8 g/case | 3.8 | 104.1 | 16.4 | 10.4 | 93.4 |
| dust formulation 16 g/case | 3.8 | 114.1 | 14.9 | 8.3 | 88.4 |

As is seen from Table 5, the treated seedlings were improved in development of fresh roots and maximum root length in comparison with the untreated seedlings.

TABLE 6

| Experimental Plot | Striking Tests Under Low Temperature Conditions | | | | |
|---|---|---|---|---|---|
| | Seedling Age | Height (mm) | Total Number of Roots | Number of Fresh Roots | Max. Root Length (mm) |
| Untreated | 3.2 | 112.9 | 13.0 | 4.4 | 20.7 |
| Treated | | | | | |
| dust formulation 4 g/case | 3.1 | 107.6 | 12.0 | 6.6 | 12.9 |
| dust formulation 8 g/case | 3.3 | 105.6 | 12.8 | 7.1 | 31.6 |
| dust formulation 16 g/case | 3.2 | 109.3 | 14.8 | 8.5 | 32.9 |

As is illustrated in Table 6, the number of fresh roots developed from the untreated seedlings was only 4.4, while those of fresh roots developed from the treated seedlings were 7 to 9 which were close to those observed under high temperature conditions. These data indicate that the treatment with the plant growth regulating compositions of the present invention is effective in encouraging rooting and striking at low temperatures.

EXAMPLE 8

Pots each of a size of 14 cm diam.×5 cm were filled with 500 g of garden soil each into which was injected 30 cc of a liquid formulation prepared as in Example 2 and diluted 500- and 5,000-fold, respectively. Thereafter, each of the pots was seeded with 20 seeds of Japanese radish (Ohkura Daikon) which were covered with soil. The radishes were grown in a greenhouse at 25° C. for 12 days, and the top weights thereof were measured to obtain the ratios between the weights of the treated and untreated radishes. The results are shown in Table 7.

TABLE 7

| Experimental Plot | Top weight (%) |
|---|---|
| Untreated | 100 |
| Treated | |
| liquid formulation diluted 500-fold | 111 |
| liquid formulation diluted 5,000-fold | 128 |

Note:
The average top weight of the untreated radishes was 903 mg.

It is apparent from Table 7 that the treatment with the liquid formulation of the present invention is effective in accelerating the growth of the tops of the radishes.

EXAMPLE 9

Seedling cases each of a size of 5×15×10 cm were filled with 500 g of garden soil each into which was injected 30 cc of 4-amino-3-methyl-1-naphthol hydrochloride solutions having an active ingredient concentration of 10 ppm and 100 ppm, respectively. Each of the cases was then seeded with 15 seeds of spinach (Heianhiyoshimaru) which were covered with soil. The spinaches were grown in a greenhouse at 25° C. for 28 days, and the top weights thereof were measured to obtain the ratios between the weights of the treated and untreated spinaches. The results are set forth in Table 8.

TABLE 8

| Concentration (ppm) | Top Weight (%) |
|---|---|
| Untreated | 100 |
| Treated | |
| 10 | 115 |
| 100 | 132 |

Note:
The average top weight of the untreated spinaches was 1.01 g.

It is to be noted from Table 8 that the treatment with 4-amino-3-methyl-1-naphthol hydrochloride solutions increases the top weights of spinaches.

EXAMPLE 10

Seedling cases each of a size of 5×15×10 cm were filled with 500 g of garden soil each into which was injected 30 cc of menadiol dinicotinate dihydrochloride solutions having an active ingredient concentration of 10 ppm and 100 ppm, respectively. The cases thus treated were each seeded with 15 seeds of Chinese cabbage (Ohzeki Hakusai) which were covered with soil. The Chinese cabbages were grown in a greenhouse at 25° C. for 14 days, and the top weights thereof were measured to obtain the ratios between the top weights of the treated and untreated Chinese cabbages. The results are shown in Table 9.

TABLE 9

| Concentration (ppm) | Top Weight (%) |
| --- | --- |
| Untreated | 100 |
| Treated | |
| 10 | 109 |
| 100 | 123 |

Note:
The average top weight of the untreated Chinese cabbage was 611 mg.

It is apparent from Table 9 that the treatment with menadiol dinicotinate dihydrochloride solutions increases the top weights of Chinese cabbages.

EXAMPLE 11

Cut chrysanthemum stalks were soaked in menadione sodium bisulfite solutions having an active ingredient concentration of 1 ppm, 10 ppm and 100 ppm, respectively, for 24 hours, then were stuck into vermiculite and were left standing in a greenhouse at 25° C. for 14 days. The rooting of the chrysanthemums was examined to obtain the ratios thereof to the rooting of the untreated chrysanthemums. The results are tabulated below.

TABLE 10

| Concentration (ppm) | Rooting Ratio (%) | Total Length of Fresh Roots (%) |
| --- | --- | --- |
| Untreated | 100 | 100 |
| Treated | | |
| 1 | 105 | 110 |
| 10 | 118 | 216 |
| 100 | 141 | 492 |

Note:
The average number of fresh roots and total length thereof developed in the untreated chrysanthemums were 11 and 25 mm, respectively.

As is indicated in Table 10, the treatment with menadione sodium bisulfite solutions is effective in encouraging rooting of chrysanthemums.

EXAMPLE 12

1 acre/200000 Wagner's pots were each charged with a 1:1 mixture of river sand and mountain sand. In the pot was sodded lawn grass (Penncross bentgrass) which had been collected with a hole cutter, and the lower portion of its thatch stratum had been then cut off to trim the roots to equal length. On the next day and 2 weeks thereafter, the lawn grass was treated with 20 cc of menadione sodium bisulfite solutions having an active ingredient concentration of 10 ppm and 100 ppm, respectively, by applying to the foliage. One month after sodding, the growth state of the roots of the lawn grass was examined to obtain the ratios between the root weights of the treated and untreated lawn grass. The results are shown in Table 11. Meanwhile the tops were trimmed every other day.

TABLE 11

| Concentration (ppm) | Air-Dry Weight of Roots (%) |
| --- | --- |
| Untreated | 100 |

TABLE 11-continued

| Concentration (ppm) | Air-Dry Weight of Roots (%) |
| --- | --- |
| Treated | |
| 10 | 172 |
| 100 | 124 |

Note:
The untreated lawn grass was sprayed only with 20 cc of water, and the air-dry weight of the roots thereof was 117 mg.

The data given in Table 11 indicate that, by spraying menadione sodium bisulfite solutions, the growth of the roots of lawn grass is apparently accelerated.

EXAMPLE 13

Nursery boxes each of a size of 30×60×5 cm were filled with particulate soil for raising seedlings as seedling beds, which soil was then sterilized. The procedure of Example 6 was then followed except that each of the boxes was seeded with 200 g of rice plant seeds (Koshihikari) which had been soaked in menadione dimethyl pyrimidinol bisulfite solutions having an active ingredient concentration of 10 ppm, 100 ppm and 1,000 ppm, respectively, at 20° C. for 48 hours and further treated with tap water at 32° C. for 24 hours to hasten germination. The young seedlings obtained 20 days after seeding were found to have the traits shown in the following Table 12.

TABLE 12

| | Traits of Young Seedlings | | |
| --- | --- | --- | --- |
| Concentration (ppm) | Height (mm) | Air-Dry Weight of Tops (mg) | Air-Dry Weight of Roots (mg) |
| Untreated | 160.4 | 17.4 | 3.4 |
| Treated | | | |
| 10 | 159.7 | 17.9 | 3.8 |
| 100 | 161.3 | 17.7 | 4.7 |
| 1000 | 157.4 | 17.3 | 4.8 |

As is apparent from Table 12, the seed soaking treatment with menadione dimethyl pyrimidinol bisulfite solutions notably accelerates the growth of the roots of rice plants although the growth of the tops thereof was not appreciably different from that of the untreated rice plants.

EXAMPLE 14

1 acre/200000 Wagner's pots were each charged with 3 litres of 1 ppm aqueous solution of a compound of the present invention the pH of which had been adjusted to 5.0. Subsequently, floating nets were spread over the surfaces of the solutions which were seeded with 40 germination-hastened rice plant seeds (Nipponbare). The rice plants were grown in a greenhouse at 25° C. for 6 days, and the heights of the seedlings thus obtained and the main root lengths were measured to obtain the ratios thereof to those of the untreated rice plants. The results are summarized in Table 13.

TABLE 13

| Compound | Increase in Height (%) | Main Root Length (%) |
| --- | --- | --- |
| 4-amino-2-methyl-1-naphthol hydrochloride | 185 | 184 |
| Menadiol tetrasodium diphosphate | 162 | 149 |
| menadiol disodium disulfate | 145 | 138 |
| 1,4-diamino-2-methyl-naphthalene dihydrochloride | 129 | 152 |
| menadiol bis(glucoside tetraacetate) | 118 | 120 |

Note:
The average height and main root length of the untreated rice plants were 2.13 cm and 5.09 cm, respectively.

As is apparent from the above data, the growths of both the tops and the roots of the treated rice plants were accelerated.

What is claimed is:

1. A method for accelerating the growth of plants which comprises applying to the foliage, roots, stems, and seeds of the plants and/or to the soil or other medium in which the plants are grown an effective plant growth accelerating amount of at least one water-soluble derivative of a vitamin K compound selected from the group consisting of
   (1) a menadione bisulfite selected from menadione sodium bisulfite and menadione dimethylpyrimidinol bisulfite,
   (2) a menadiol inorganic acid ester salt selected from menadiol tetrasodium diphosphate and menadiol disodium disulfate,
   (3) menadiol dinicotinate dihydrochloride,
   (4) menadiol bis(glucoside tetraacetate),
   (5) 4-amino-2-methyl-1-naphthol hydrochloride,
   (6) 4-amino-3-methyl-1-naphthol hydrochloride, and
   (7) 1,4-diamino-2-methylnaphthalene dihydrochloride.

2. A method according to claim 1 wherein the water-soluble derivative of a vitamin K compound is a menadione bisulfite selected from menadione sodium bisulfite and menadione dimethylpyrimidinol bisulfite.

3. A method according to claim 1 wherein the water-soluble derivative of a vitamin K compound is a menadiol inorganic acid ester salt selected from menadiol tetrasodium diphosphate and menadiol disodium disulfate.

4. A method according to claim 1 wherein the water-soluble derivative of a vitamin K compound is a menadiol dinicotinate dihydrochloride.

5. A method according to claim 1 wherein the water-soluble derivative of a vitamin K compound is a menadiol bis(glucoside tetraacetate).

6. A method according to claim 1 wherein the water-soluble derivative of a vitamin K compound is a 4-amino-2-methyl-1-naphthol hydrochloride.

7. A method according to claim 1 wherein the water-soluble derivative of a vitamin K compound is a 4-amino-2-methyl-1-naphthol hydrochloride.

8. A method according to claim 1 wherein the water-soluble derivative of a vitamin K compound is a 1,4-diamino-2-methylnaphthalene dihydrochloride.

9. A method according to claim 1 wherein the water-soluble derivative of a vitamin K compound is a applied at a rate of from 2 to 20,000 g. per acre.

* * * * *